(12) United States Patent
Feher et al.

(10) Patent No.: US 7,579,518 B2
(45) Date of Patent: Aug. 25, 2009

(54) PLANTS HAVING IMPROVED SEED YIELD AND EXPRESSING A NUCLEIC ACID ENCODING A SMALL SUBUNIT RIBOSOMAL (S3A) PROTEIN AND METHOD FOR MAKING THE SAME

(75) Inventors: Attila Feher, Szeged (HU); Denes Dudits, Szeged (HU); Valerie Frankard, Rhode-St-Genese (BE)

(73) Assignee: Cropdesign N.V., Zwijnaarde (BE)

( * ) Notice: Subject to any disclaimer, the term of this patent is extended or adjusted under 35 U.S.C. 154(b) by 0 days.

(21) Appl. No.: 11/084,250

(22) Filed: Mar. 21, 2005

(65) Prior Publication Data

US 2005/0210544 A1 Sep. 22, 2005

Related U.S. Application Data

(60) Provisional application No. 60/556,847, filed on Mar. 26, 2004.

(30) Foreign Application Priority Data

Mar. 22, 2004 (EP) .................................. 04101179

(51) Int. Cl.
C12N 15/82 (2006.01)
(52) U.S. Cl. ...................................................... 800/290
(58) Field of Classification Search ........................ None
See application file for complete search history.

(56) References Cited

U.S. PATENT DOCUMENTS

| 2003/0041343 | A1* | 2/2003 | Tao et al. ..................... 800/278 |
| 2003/0074687 | A1* | 4/2003 | Scott ........................... 800/278 |
| 2006/0150283 | A1* | 7/2006 | Alexandrov et al. ......... 800/288 |

FOREIGN PATENT DOCUMENTS

| EP | 1 033 405 A2 | 9/2000 |
| WO | WO 00/56905 | 9/2000 |

OTHER PUBLICATIONS de Pater et al. The promoter of the rice gene GOS2 is active in various different monocot tissues and binds rice nuclear factor ASF-1. (1992) The Plant Journal, vol. 2, pp. 837-844.*
Lazar et al. Transforming growth factoer alpha: mutation of aspartic acid 47 and leucine 48 results in different biological activities. (1988) Mol. Cell. Biol. vol. 8; pp. 1247-1252.*
Hill et al. Functional analysis of conserved histidines in ADP-glucose pyrophosphorylase from *Escherichia coli*. (1998) Biochem. Biophys. Res. Comm. vol. 244; pp. 573-577.*
Van Beest et al. Drosophila RpS3a, a novel Minute gene situated between the segment polarity genes cubitus interruptus and dTCF. (1998) Nucleic Acids Research; vol. 26, pp. 4471-4475.*
Guo et al. Protein tolerance to random amino acid change. (2004) Proc. Natl. Acad. Sci. USA; vol. 101; pp. 9205-9210.*
Cordeiro-Da-Silva et al. Dual role of the Leishmania major ribosomal protein S3a homologue in regulation of T- and B-Cell activation. (2001) Infection and Immunity; vol. 69, pp. 6588-6596.*
Cui et al. Novel interaction between the transcription factor CHOP (GADD153) and the ribosomal protein FTE/S3a modulates erythorpoeisis. (2000) JBC; vol. 275, pp. 7591-7596.*
Lecomte et al. The S3a ribosomal protein gene is identical to the Fte-1 (v-fos transformation effector) gene and the TNF-alpha-induced TU-II gene, and its transcript level is altered in transformed and tumor cells. (1997) Gene; vol. 186, pp. 271-277.*
Giddings; Transgenic plants as protein factories. (2001) Current Opinion in Biotech; vol. 12, pp. 450-454.*
Sell S. Cancer Markers of the 1990s (1990) in Clinics in Laboratory Medicine vol. 10, editors: Gorstein and Thor; pp. 1-37.*
Newman et al (1998) GenBank Accession AJ001342; pp. 1-2.*
Chan et al. The primary structures of rat ribosomal proteins S3a (The V-Fos transformation effector) and of S3b. (1996) Biochem. And Biophys. Res. Comm.; vol. 228, pp. 141-147.*
Barakat et al, "The Organization of Cytoplasmic Ribosomal Protein Genes in the Arabidopsis Genome", Plant Physiology, Oct. 2001, vol. 127, pp. 398-415.
Di et al, "Expression of a Truncated Form of Ribosomal Protein L3 Confers Resistance to Pokeweek Antiviral Protein and the *Fusarium* Mycotoxin Deoxynivalenol", Molecular Plant-Microbe Interactions, vol. 18, No. 8, 2005, pp. 762-770.
Xu et al, "Characterization of a rice gene family encoding root-specific proteins", Plant Molecular Biology 27:237-248, 1995.
Lyamouri et al, "Organization, sequence, and phylogenetic analysis of the *ribosomal protein S3* gene from *Drosophila virilis*", Gene 294 (2002) 147-156.

* cited by examiner

*Primary Examiner*—Cathy Kingdon Worley
(74) *Attorney, Agent, or Firm*—Nixon & Vanderhye P.C.

(57) ABSTRACT

The present invention concerns a method for improving the growth characteristics of plants by introducing and expressing in a plant a nucleic acid encoding a small subunit ribosomal (S3a) protein. The invention also relates to transgenic plants having introduced therein a nucleic acid encoding an S3a protein, which plants have improved growth characteristics relative to corresponding wild type plants. The improved growth characteristics are particularly increased seed yield compared to corresponding wild type plants, in particularly increased number of filled seeds, increased total seed weight, increased harvest index and increased thousand kernel weight. The present invention also concerns constructs useful in the methods of the invention.

10 Claims, 4 Drawing Sheets

FIGURE 1

SEQ ID NO 1: CDS0730 coding sequence (start and stop in bold)

atggctgtcgggaagaacaagaggatttcaaagggtaggaaaggaggaaagaagaaggctgt
tgatcccttctccaagaaggattggtatgacgtgaaggctcctggttctttcacgaacagga
atgttgggaagactcttgtttccaggactcagggtaccaagattgcctctgagggactgaaa
cacagggtgtttgaggtttctcttgctgatctacaaaatgatgaggataatgcctacaggaa
gatccgtcttagagctgaagatgttcagggaaggaatgtgttgacccagttctggggtatgg
atttcacaaccgacaagctaaggtcattggtgaagaagtggcagactttgattgaagcccat
gtcgatgtgaaaaccacagacggctacaccttgaggatgttctgcatcgccttcacaaagag
acgtgctaaccaagtgaagcgtacctgttacgctcaatccagccaaatccgtcagatccgca
gaaagatgagtgagattatggtgaaggaggcttcatcttgtgacctcaaggagctagtggcc
aagttcatcccagaggccattggaagagagattgagaaggcaacacagggcatctacccgtt
gcagaatgtgttcatccgtaaagtgaagatcctaaaggctcccaagtttgaccttggaaagc
tcatggaggtgcatggagattacacagcagaggatgttggtgtgaaggtagacaggccagct
gatgagacaatggttgaggagccaacagaaatcatcggagcttaggggattatagatttgtt
tgttttttcgctggcaaaaaaaa

SEQ ID NO 2: CDS0730 protein sequence

MAVGKNKRISKGRKGGKKKAVDPFSKKDWYDVKAPGSFTNRNVGKTLVSRTQGTKIASEGLK
HRVFEVSLADLQNDEDNAYRKIRLRAEDVQGRNVLTQFWGMDFTTDKLRSLVKKWQTLIEAH
VDVKTTDGYTLRMFCIAFTKRRANQVKRTCYAQSSQIRQIRRKMSEIMVKEASSCDLKELVA
KFIPEAIGREIEKATQGIYPLQNVFIRKVKILKAPKFDLGKLMEVHGDYTAEDVGVKVDRPA
DETMVEEPTEIIG A

FIGURE 3A

SEQ ID NO 3: Saccharum officinarum: DNA sequence (start and stop in bold)

aagatgaagcctttgtcatggtgcatgctaaagatgctgaggctgagaagttgagggatgaa
ccatgacaaaggcttcatctttctcgacctgaatcctgtccacattcccttcagcatcttc
aattcagcctcgatcatttcttcttaagcaccccgccgtcgttctcttcctgcatccccgc
cccattccctagcgtcgccccctcgccgccgcacggacgcagcgacgagctctcgcagcag
caatggcggttggcaagaataagcgtatctccaagggcaagaagggaggcaagaagaagacc
gtggatccgttcagcaaaaaggattggtatgatatcaaggctccgtcggtcttcagcgtgcg
caacatcggcaagaccctggtctccaggacacagggcaccaagattgcctctgagggtttaa
agcacagagtatttgaggtctccttggctgatcttcagagtgatgaagaccaggcgtacagg
aagatcagacttcgtgcagaggatgtacaagggagaaatgttctcacaaacttctggggtat
gagcttcaccaccgacaagctccgttcacttgtgaagaagtggcagacgcttattgaggctc
atgttgatgtcaagaccaccgataactatatgctgcggctgttctgcattgggttcaccaag
aggcggcccaatcaagtgaagcgcacttgctatgctcaagcaagccaaatcagacagattcg
tcggaagatgactgaaatcatgagcaaccaagcttcaacttgtgatctgaaagagctcgtgt
ccaagttcatccctgaggtcattggaaaggaaatcgagaaagccacctctagcatattcccc
ttgcaaaatgtcttcatccgcaaggtgaagatcctgaaagcaccaaagttcgacattggaaa
gctcatggaggtccatggtgactatgccaaggaggatgttggtgtcaagatggacaggcctg
ctgaaggcgacgaggccatgggaggacaggaggttgctgcagctgagtgattagtctcactg
tttacgtccgagttagagctgccatatttccttgaaacacttaggaacactttttttgagag
tctgacatgtggtggcttcgattctccttgaaaatttgcagcatgggaaatgt

SEQ ID NO 4: Saccharum officinarum: protein sequence

MAVGKNKRISKGKKGGKKKTVDPFSKKDWYDIKAPSVFSVRNIGKTLVSRTQGTKIASEGLK
HRVFEVSLADLQSDEDQAYRKIRLRAEDVQGRNVLTNFWGMSFTTDKLRSLVKKWQTLIEAH
VDVKTTDNYMLRLFCIGFTKRRPNQVKRTCYAQASQIRQIRRKMTEIMSNQASTCDLKELVS
KFIPEVIGKEIEKATSSIFPLQNVFIRKVKILKAPKFDIGKLMEVHGDYAKEDVGVKMDRPA
EGDEAMGGQEVAAAE

SEQ ID NO 5: Artificial sequence prm02255 (AttB1 site in italic)

*GGGGACAAGTTTGTACAAAAAAGCAGGCTTCAC*AATGGCTGTCGGGAAGAA

SEQ ID NO 6: Artificial sequence prm02256 (AttB2 site in italic)

*GGGGACCACTTTGTACAAGAAAGCTGGGT*CCTAAGCTCCGATGATTTCT

FIGURE 3B

PLANTS HAVING IMPROVED SEED YIELD AND EXPRESSING A NUCLEIC ACID ENCODING A SMALL SUBUNIT RIBOSOMAL (S3A) PROTEIN AND METHOD FOR MAKING THE SAME

This application claims benefit of U.S. Provisional Application No. 60/556,847, filed 26 Mar. 2004 and EP04101179.2, filed 22 Mar. 2004; the entire contents of each of which is incorporated herein by reference.

The present invention relates generally to the field of molecular biology and concerns a method for improving plant growth characteristics. More specifically, the present invention concerns a method for improving plant growth characteristics, particularly yield, by introducing and expressing in a plant a nucleic acid encoding an S-phase specific ribosomal protein (S3A). The present invention also concerns plants having introduced therein an S3A-encoding nucleic acid, which plants have improved growth characteristics relative to corresponding wild type plants.

The ever-increasing world population and the dwindling supply of arable land available for agriculture fuel agricultural research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits. A trait of particular economic interest is yield. Yield is normally defined as the measurable produce of economic value from a crop. This may be defined in terms of quantity and/or quality. Yield is directly dependent on several factors, for example, the number and size of the organs, plant architecture (for example, the number of branches), seed production and more. Root development, nutrient uptake and stress tolerance are also important factors in determining yield. Crop yield may be increased by optimizing one of the abovementioned factors.

An outline of the ribosome assembly pathway emerged from sucrose gradient analyses in the early 1970s. These studies identified three major pre-ribosomal particles. An early 90S particle ('S' being the rate of sedimentation) is subsequently processed into 66S and 43S pre-ribosomes, the precursors to the mature 60S and 40S subunits, respectively. The 60S subunit, after processing, is composed of 25S, 5.8S and 5S ribosomal RNA. A number of proteins will have interacted along the maturation process to yield the final structure. The 40S subunit is composed of an 18S ribosome RNA, and again a number of proteins will have interacted before the mature complex is ready. These two subunits assemble into a large complex in which the small subunit 40S binds the mRNA and the tRNAs, while the large subunit catalyzes peptide bond formation. About ⅔ of the mass of the ribosome consists of RNA and ⅓ of protein. The proteins are named in accordance with the subunit of the ribosome to which they belong: the small subunit (S1 to S31) and the large subunit (L1 to L44). Most of the proteins interact with multiple RNA elements, often from different domains, to organize and stabilize the rRNA tertiary structure. While the crucial activities of decoding and peptide transfer are RNA based processes, proteins play an active role in functions that may have evolved to streamline the process of protein synthesis. In addition to their function in the ribosome, many ribosomal proteins have some function 'outside' the ribosome.

S3A (cyc07) was first cloned in 1991. It encodes a 40S ribosomal protein (small subunit) and is homologous to v-fos transformation effector (encoded by the fte-1 gene in humans and rats), the TNF-alpha-induced TU-11 gene in mice, and is similar to the yeast PLC1 and PLC2. The expressions of mammalian fte-1, plant cyc-07 and yeast PLC2 have all been shown to be cell-cycle-regulated and involved in protein synthesis at the level of the ribosome.

The ability to improve various growth characteristics of a plant, would have many applications in areas such as crop enhancement, plant breeding, in the production of ornamental plants, aboriculture, horticulture, forestry, the production of algae for use in bioreactors (for the biotechnological production of substances such as pharmaceuticals, antibodies, or vaccines, or for the bioconversion of organic waste) and other such areas.

It has now been found that introduction and expression in a plant of a nucleic acid encoding an S-phase specific ribosomal protein (S3A) gives plants having improved growth characteristics relative to corresponding wild type plants. Therefore according to one embodiment of the present invention there is provided a method for improving the growth characteristics of a plant, comprising introduction and expression in a plant of a nucleic acid encoding a S3A.

Advantageously, performance of the methods according to the present invention result in plants having a variety of improved growth characteristics, especially increased yield, particularly seed yield. More specifically, such improved growth characteristics include increased number of (filled) seeds, increased seed weight, increased harvest index and increased thousand kernel weight (TKW).

The term "increased yield" as defined herein is taken to mean an increase in any one or more of the following, each relative to corresponding wild type plants: (i) increased biomass (weight) of one or more parts of a plant, particularly aboveground (harvestable) parts, increased root biomass or increased biomass of any other harvestable part; (ii) increased seed yield, which includes an increase in seed biomass (seed weight) which may be an increase in the seed weight per plant or on an individual seed basis; (iii) increased number of (filled) seeds; (iv) increased seed size, which may also influence the composition of seeds; (v) increased seed volume, which may also influence the composition of seeds; (vi) increased harvest index, which is expressed as a ratio of the yield of harvestable parts, such as seeds, over the total biomass; and (vii) increased thousand kernel weight (TKW), which is extrapolated from the number of filled seeds counted and their total weight. An increased TKW may result from an increased seed size and/or seed weight.

According to a preferred embodiment of the invention, the increase in yield encompasses an increase in yield on a seed level as defined in any one or more of (ii) to (vii) above.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, among others. Taking rice as an example, a yield increase may be manifested by an increase in one or more of the following: number of plants per hectare or acre, number of panicles per plant, number of spikelets per panicle, number of flowers per panicle, increase in the seed filling rate, increase in thousand kernel weight, among others. An increase in yield may also result in modified architecture, or may occur as a result of modified architecture.

According to a preferred feature of the present invention, performance of the methods of the invention result in plants having modified yield which is manifested by at least one of: increased TKW, increased number of (filled) seeds, increased seed weight and increased harvest index, each relative to control plants. Therefore, according to the present invention, there is provided a method for increasing plant yield, which method comprises introduction and expression in a plant of a nucleic acid encoding a S3A polypeptide.

Since the transgenic plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant (including seeds), or may be throughout substantially the whole plant. A plant having an increased growth rate may even exhibit early flowering. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible. If the growth rate is sufficiently increased, it may allow for the sowing of further seeds of the same plant species (for example sowing and harvesting of rice plants followed by sowing and harvesting of further rice plants all within one conventional growing period). Similarly, if the growth rate is sufficiently increased, it may allow for the sowing of further seeds of different plants species (for example the sowing and harvesting of rice plants followed by, for example, the sowing and optional harvesting of soy bean, potatoes or any other suitable plant). Harvesting additional times from the same rootstock in the case of some plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves plotting growth experiments, such parameters may be: T-Mid (the time taken for plants to reach 50% of their maximal size) and T-90 (time taken for plants to reach 90% of their maximal size), amongst others.

Performance of the methods of the invention gives plants having an increased growth rate. Therefore, according to the present invention, there is provided a method for increasing the growth rate of plants, which method comprises introduction and expression in a plant of a nucleic acid encoding a S3A polypeptide. An increase in growth rate is exemplified herein by an increase in TKW, increased number of (filled) seeds, increased seed weight and increased harvest index, each relative to control plants/corresponding wild-type plants.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the typical stresses to which a plant may be exposed. These stresses may be the everyday biotic and/or abiotic (environmental) stresses to which a plant is exposed. Typical abiotic or environmental stresses include temperature stresses caused by atypical hot or cold/freezing temperatures; salt stress; water stress (drought or excess water). Abiotic stresses may also be caused by chemicals. Biotic stresses are typically those stresses caused by pathogens, such as bacteria, viruses, fungi and insects.

The abovementioned growth characteristics may advantageously be modified in any plant.

The term "plant" as used herein encompasses whole plants, ancestors and progeny of the plants and plant parts, including seeds, shoots, stems, leaves, roots (including tubers), and tissues and organs, wherein each of the aforementioned preferably comprise the gene of interest. The term "plant" also encompasses embryos, meristematic regions, gametophytes, sporophytes, pollen, and microspores, again wherein each of the aforementioned preferably comprise the gene of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Omithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthria* fleckii, Pogonarthria squarrosa, Populus spp., Prosopis cineraria, Pseudotsuga menziesii, Pterolobium stellatum, Pyrus communis, Quercus spp., Rhaphiolepsis umbellata, Rhopalostylis sapida, Rhus natalensis, Ribes grossularia, Ribes spp., Robinia pseudoacacia, Rosa spp., Rubus spp., Salix spp., Schyzachyrium sanguineum, Sciadopitys verticillata, Sequoia sempervirens, Sequoiadendron giganteum, Sorghum bicolor, Spinacia spp., Sporobolus fimbriatus, Stiburus alopecuroides, Stylosanthos humilis, Tadehagi spp, Taxodium distichum, Themeda triandra, Trifolium spp., Triticum spp., Tsuga heterophylla, Vaccinium spp., Vicia spp., Vitis vinifera, Watsonia pyramidata, Zantedeschia aethiopica, Zea mays, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash, tea and algae, amongst others. According to a preferred embodiment of the present invention, the plant is a crop plant such as soybean, sunflower, canola, alfalfa, rapeseed, cotton, tomato, potato or tobacco. Further preferably, the plant is a monocotyledonous plant, such as sugar cane. More preferably the plant is a cereal, such as rice, maize, wheat, barley, millet, rye, sorghum or oats.

An S3A may easily be identified by aligning a query sequence (preferably a protein sequence) with known S3A protein sequences (see for example the alignment shown in FIG. 1). The query sequence may be aligned (with known S3A sequences) using, for example, the VNTI AlignX multiple alignment program (InforMax, Bethesda, Md.), with default settings for gap opening penalty of 10 and a gap extension of 0.05. Since S3A sequences are highly conserved, a person skilled in the art would readily be able to identify other S3A sequences by comparing any conserved regions of the query sequence against those of the known S3A sequences. S3As have also been shown to bind to eukaryotic initiation factors eIF-2 and eIF-3.

The term "S3A" as defined herein is taken to mean a nucleic sequence as represented by SEQ ID NO: 1 and to variants thereof as described hereinafter or to an amino acid sequence as represented by SEQ ID NO: 2 and to variants thereof as described hereinafter.

The nucleic acid to be introduced into a plant is preferably the nucleic acid represented by SEQ ID NO: 1 or is a variant of SEQ ID NO: 1, as described hereinafter. The nucleic acid is preferably operably linked to a constitutive promoter for overexpression in a plant. The constitutive promoter is preferably a GOS2 promoter, further preferably a GOS2 promoter from rice. It should be clear that the applicability of the present invention is not restricted to the S3A represented by SEQ ID NO: 1, nor is the applicability of the invention restricted to expression of an S3A gene/nucleic acid when driven by a GOS2 promoter.

According to a preferred aspect of the present invention, enhanced or increased expression of the S3A nucleic acid is envisaged. Methods for obtaining enhanced or increased expression of genes or gene products are well documented in the art and include, for example, overexpression driven by a strong promoter, the use of transcription enhancers or translation enhancers.

The nucleic acid encoding an S3A may be derived from any source provided that the nucleic acid, when expressed in a plant, leads to modulated S3A gene expression and/or modulated levels and/or activity of an S3A polypeptide. The nucleic acid/gene encoding an S3A may be isolated from a microbial source, such as bacteria, yeast or fungi, or from a plant, algae or animal (including human) source. This nucleic acid may be modified from its native form in composition and/or genomic environment through deliberate human manipulation. The nucleic acid is preferably a homologous nucleic acid, i.e. a nucleic acid obtained from a plant, whether from the same plant species in which it is to be introduced or whether from a different plant species. The nucleic acid may be isolated from a dicotyledonous species, preferably from the family Brassicaceae, further preferably from *Arabidopsis thaliana*. More preferably, the S3A isolated from *Arabidopsis thaliana* is represented by SEQ ID NO: 1 and the amino acid sequence as represented by SEQ ID NO: 2.

The sequence represented by SEQ ID NO: 1 depicts an S3A from *Arabidopsis thaliana*, with SEQ ID NO: 2 being the corresponding amino acid sequence. Advantageously, the applicability of the present invention is not restricted to the use of an S3A from *Arabidopsis* as represented by SEQ ID NO: 1. The methods according to the present invention may also be practised using variants of the nucleic acid represented by SEQ ID NO: 1 or variants of the amino acid sequence represented by SEQ ID NO: 2.

Suitable variant nucleic acid and amino acid sequences useful in practising the method according to the invention, include:
  (i) Portions of a nucleic acid represented by the sequence of SEQ ID NO: 1;
  (ii) Sequences capable of hybridising to a nucleic acid represented by the sequence of SEQ ID NO: 1;
  (iii) Alternative splice variants of a nucleic acid represented by the sequence of SEQ ID NO: 1;
  (iv) Allelic variants of a nucleic acid represented by the sequence of SEQ ID NO: 1; and
  (v) Homologues, derivatives and active fragments of an amino acid represented by the sequence of SEQ ID NO: 2.

It will be apparent to a person skilled in the art that the use of the full length S3A DNA sequence would not be a prerequisite to carrying out the methods according to the invention. The methods according to the invention may advantageously be practised using portions of the S3A-encoding DNA/nucleic acid represented by SEQ ID NO: 1. A portion refers to a piece of DNA derived or prepared from an original (larger) DNA molecule, which DNA portion, when introduced into a plant, gives plants having modified growth characteristics. A portion may be prepared, for example, by making one or more deletions to the nucleic acid sequence of SEQ ID NO: 1 using techniques well known in the art.

Therefore according to the invention, there is provided, a method for improving the growth characteristics of plants, comprising introduction and expression in a plant of a portion of a nucleic acid as represented by SEQ ID NO: 1.

Another variant sequence of SEQ ID NO: 1 is a nucleic acid capable of hybridising with a sequence represented by SEQ ID NO: 1. Advantageously, the methods according to the present invention may also be practised using sequences that hybridise to SEQ ID NO: 1.

The term "hybridisation" as defined herein is a process wherein substantially homologous complementary nucleotide sequences anneal to each other. The hybridisation process can occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process can also occur with one of the complementary nucleic acids immobilised to a matrix such as magnetic beads, Sepharose beads or any other resin.

Tools in molecular biology relying on such a process include the isolation of poly (A⁺) mRNA. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. Hybridisation preferably occurs under stringent conditions. Stringent conditions are those that (1) employ low ionic strength and high temperature for washing, for example, 0.5M sodium phosphate buffer pH 7.2, 1 mM EDTA pH 8.0 in 7% SDS at either 65° C. or 55° C., or (2) employ during hybridization a denaturing agent such as formamide, for example, 50% (vol/vol) formamide with 0.1% bovine serum albumin, 0.1% Ficoll, 0.1% polyvinylpolypyrrolidone, 0.05 M sodium phosphate buffer at pH 6.5 with 0.75 M NaCl, 0.075 M sodium citrate at 42° C. A specific example includes the use of 50% formamide, 5×SSC (0.75 M NaCl, 0.075 M sodium citrate), 50 mM sodium phosphate (pH 6.8), 0.1% sodium pyrophosphate, 5× Denhard's solution, sonicated salmon sperm DNA (50 nm/ml), 0.1% SDS and 10% dextran sulfate at 55° C., with washes at 55° C. in 0.2×SSC and 0.1% SDS. A skilled person can readily determine and vary the stringency conditions appropriately to obtain a clear and detectable hybridization signal.

Therefore according to the invention, there is provided, a method for improving the growth characteristics of plants, comprising introduction and expression in a plant of a sequence capable of hybridising under stringent conditions to a nucleic acid sequence as represented by SEQ ID NO: 1.

Another variant useful in the methods of the invention is an alternative splice variant of a nucleic acid as represented by the sequence of SEQ ID NO: 1. The term "alternative splice variant" as used herein encompasses variants of a nucleic acid sequence in which selected introns and/or exons have been excised, replaced or added. Such variants will be ones in which the biological activity of the protein remains unaffected, which can be achieved by selectively retaining functional segments of the protein. Such splice variants may be found in nature or may be manmade. Methods for making such splice variants are well known in the art.

Therefore, the invention also provides a method for improving the growth characteristics of plants, comprising introduction and expression in a plant of an alternative splice variant of a nucleic acid as represented by SEQ ID NO: 1.

Another variant useful in the methods of the invention is an allelic variant of a nucleic acid as represented by the sequence of SEQ ID NO: 1. Allelic variants exist in nature and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

Therefore, the invention also provides a method for improving the growth characteristics of plants, comprising introduction and expression in a plant of an allelic variant of a nucleic acid as represented by SEQ ID NO: 1.

Further advantageously, the methods according to the present invention may also be practised using homologues, derivatives or active fragments of an S3A as represented by SEQ ID NO: 2. Nucleic acids encoding homologues, derivatives or active fragments of an amino acid as represented by SEQ ID NO: 2 may readily be determined using routine techniques well known to persons skilled in the art. Such nucleic acids suitable for use in the methods of the invention may readily be determined as described hereinbefore.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company).

The homologues useful in the method according to the invention have in increasing order of preference at least 55%, 60%, 65%, 70%, 75%, 80%, 85%, 90%, 95% sequence identity to the amino acid sequence as represented by SEQ ID NO: 2.

Also encompassed by the term "homologues" are two special forms of homology, which include orthologous sequences and paralogous sequences, which encompass evolutionary concepts used to describe ancestral relationships of genes. The term "paralogous" relates to gene-duplications within the genome of a species leading to paralogous genes. The term "orthologous" relates to homologous genes in different organisms due to ancestral relationship.

Othologues in, for example, monocot plant species may easily be found by performing a so-called reciprocal blast search. This may be done by a first blast involving blasting the sequence in question (for example, SEQ ID NO: 1 or SEQ ID NO: 2) against any sequence database, such as the publicly available NCBI database which may be found at: URL: ncbi nlm nih gov. If orthologues in rice were sought, the sequence in question would be blasted against, for example, the 28,469 full-length cDNA clones from *Oryza sativa* Nipponbare available at NCBI. BLASTn may be used when starting from nucleotides or TBLASTX when starting from the protein, with standard default values (expectation 10, alignment 50). The blast results may be filtered. The full-length sequences of either the filtered results or the non-filtered results are then blasted back (second blast) against the sequence in question (SEQ ID NO: 1 or 2). The results of the first and second blasts are then compared. In the case of large families, ClustalW is used followed by a neighbour joining tree to help visualize the clustering.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues, and deletions will range from about 1 to 20 residues. Preferably, amino acid substitutions comprise conservative amino acid substitutions.

A homologue may also be in the form of an "insertional variant" of a protein, i.e. where one or more amino acid residues are introduced into a predetermined site in a protein. Insertions may comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)6-tag, glutathione S-transferase-tag, protein A, maltose-binding protein, dihydrofolate reductase, Tag-100 epitope, c-myc epitope, FLAG®-epitope, lacZ, CMP (calmodulin-binding peptide), HA epitope, protein C epitope and VSV epitope.

Homologues in the form of "deletion variants" of a protein are characterised by the removal of one or more amino acids from a protein.

Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

"Derivatives" include peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in SEQ ID NO: 2. "Derivatives" of a protein encompass peptides, oligopeptides, polypeptides, proteins and enzymes which may comprise naturally occurring altered, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

"Active fragments" of an S3A protein encompasses at least five contiguous amino acid residues of a protein, which residues retain similar biological and/or functional activity to the naturally occurring protein.

Methods for the search and identification of S3A homologues would be well within the realm of a person skilled in the art. Methods for the alignment of sequences for comparison are well known in the art, such methods include GAP, BESTFIT, BLAST, FASTA and TFASTA. GAP uses the algorithm of Needleman and Wunsch (J. Mol. Biol. 48: 443-453, 1970) to find the alignment of two complete sequences that maximises the number of matches and minimises the number of gaps. The BLAST algorithm calculates percent sequence identity and performs a statistical analysis of the similarity between the two sequences. The software for performing BLAST analysis is publicly available through the National Centre for Biotechnology Information. Homologues suitable for use in the methods of the invention, i.e. those having at least 55% sequence identity to the amino acid sequence represented by SEQ ID NO: 2, may be identified by taking full length protein sequences and aligning them using the VNTI AlignX multiple alignment program (InforMax, Bethesda, Md.), with default settings for gap opening penalty of 10 and a gap extension of 0.05. See for example FIG. 1.

Therefore, the invention also provides a method for modifying the growth characteristics of plants, comprising modulating expression in a plant of a nucleic acid encoding a homologue, derivative or active fragment of a S3A as represented by SEQ ID NO: 2, which homologue, derivative or active fragment has in increasing order of preference at least 55%, 60%, 65%, 70%, 75%, 80%, 85%, 90%, 95% sequence identity to an amino acid sequence as represented by SEQ ID NO: 2.

The invention also provides genetic constructs and vectors to facilitate introduction and/or expression of the nucleotide sequences useful in the methods according to the invention.

Therefore, there is provided a gene construct comprising:
(i) a nucleic acid as represented by SEQ ID NO: 1 or a variant thereof (as defined hereinabove), which encodes an S3A polypeptide as represented by SEQ ID NO: 2 or a variant thereof (as defined hereinabove);
(ii) one or more control sequences capable of driving expression of the nucleic acid sequence of (i); and optionally
(iii) a transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

Plants are transformed with a vector comprising the sequence of interest (i.e., a nucleic acid as represented by SEQ ID NO: 1 or a variant thereof (as defined hereinabove)). The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence depending on the desired outcome. For example, a meristem-specific promoter, such as the rnr (ribonucleotide reductase), cdc2a promoter and the cyc07 promoter, may be used to effect expression in all growing parts of the plant, thereby increasing cell proliferation, which in turn would increase yield or biomass. If the desired outcome would be to influence seed characteristics, such as the storage capacity, seed size, seed number, biomass etc., then a seed-specific promoter, such as p2S2, pPROLAMIN, pOLEOSIN may be selected. An aleurone-specific promoter may be selected in order to increase growth at the moment of germination, thereby increasing the transport of sugars to the embryo. An inflorescence-specific promoter, such as pLEAFY, may be utilised if the desired outcome would be to modify the number of flower organs. To produce male-sterile plants one may use an anther specific promoter. To influence flower architecture, for example petal size, one may choose a petal-specific promoter. If the desired outcome would be to modify growth and/or developmental characteristics in particular organs, then the choice of the promoter would depend on the organ to be modified. For example, use of a root-specific promoter may lead to increased growth and/or increased biomass or yield of the root and/or phenotypic alteration of the root. This may be particularly important where it is the root itself that is the desired end product; such crops include sugar beet, turnip, carrot and potato. A fruit-specific promoter may be used to modify, for example, the strength of the outer skin of the fruit or to increase the size of the fruit. A green tissue-specific promoter may be used to increase leaf size. A cell wall-specific promoter may be used to increase the rigidity of the cell wall, thereby increasing pathogen resistance. An anther-specific promoter may be used to produce male-sterile plants. A vascular-specific promoter may be used to increase transport from leaves to seeds. A nodule-specific promoter may be used to increase the nitrogen fixing capabilities of a plant, thereby increasing nutrient levels in a plant. A stress-inducible promoter may also be used to drive expression of a nucleic acid to increase membrane integrity during conditions of stress. A stress inducible promoter such as the water stress induced promoter WSI18, the drought stress induced Trg-31 promoter, the ABA related promoter rab21 or any other promoter which is induced under a particular stress condition, such as temperature stress (cold, freezing, heat), osmotic stress, drought stress, oxidative stress or biotic stress may be used to drive expression of an S3A gene.

Preferably, the nucleic acid encoding an S3A as represented by SEQ ID NO: 1 or a functional variant thereof, as hereinbefore described, is operably linked to a constitutive promoter. The term "constitutive" as defined herein refers to a promoter that is expressed predominantly in more than one tissue or organ and predominantly at any stage in the life cycle of a plant. Preferably, the constitutive promoter is expressed predominantly throughout the plant. Preferably, the constitutive promoter is the GOS2 promoter from rice.

Examples of other constitutive promoters suitable for use in the methods of the invention are listed in Table A below.

TABLE A

Examples of constitutive promoters for use in performance of the invention

| GENE SOURCE | EXPRESSION PATTERN | REFERENCE |
| --- | --- | --- |
| Actin | constitutive | McElroy et al, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant. 100: 456-462, 1997 |

TABLE A-continued

Examples of constitutive promoters for use in performance of the invention

| GENE SOURCE | EXPRESSION PATTERN | REFERENCE |
| --- | --- | --- |
| GOS2 | constitutive | de Pater et al, Plant J Nov; 2(6): 837-44, 1992 |
| ubiquitin | constitutive | Christensen et al, Plant Mol. Biol. 18: 675-689, 1992 |
| rice cyclophilin | constitutive | Buchholz et al, Plant Mol Biol. 25(5): 837-43, 1994 |
| maize H3 histone | constitutive | Lepetit et al, Mol. Gen. Genet. 231: 276-285, 1992 |
| actin 2 | constitutive | An et al, Plant J. 10(1); 107-121, 1996 |

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences which may be suitable for use in performing the invention. Such sequences would be known or may readily be obtained by a person skilled in the art.

The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of the invention. Suitable markers may be selected from markers that confer antibiotic or herbicide resistance. Cells containing the recombinant DNA will thus be able to survive in the presence of antibiotic or herbicide concentrations that kill untransformed cells. Examples of selectable marker genes include the bar gene which provides resistance to the herbicide Basta; the npt gene which confers resistance to the antibiotic kanamycin; the hpt gene which confers hygromycin resistance. Visual markers, such as the Green Fluorescent Protein (GFP, Haseloff et al., 1997), β-glucuronidase (GUS) or luciferase may also be used as selectable markers. Further examples of suitable selectable marker genes include the ampicillin resistance (Ampr), tetracycline resistance gene (Tcr), bacterial kahamycin resistance gene (Kanr), phosphinothricin resistance gene, neomycin phosphotransferase gene (nptll), hygromycin resistance gene, gene, and the chloramphenicol acetyltransferase (CAT) gene, amongst others.

The present invention also encompasses plants obtainable by the methods according to the present invention. The present invention therefore provides plants obtainable by the method according to the present invention, which plants have introduced therein a nucleic acid encoding an S3A protein.

The invention also provides a method for the production of transgenic plants having improved growth characteristics, comprising introduction and expression in a plant of a nucleic acid as represented by SEQ ID NO: 1 or a variant thereof (as defined hereinabove).

More specifically, the present invention provides a method for the production of transgenic plants having improved growth characteristics, which method comprises:
   (i) introducing into a plant or plant cell a nucleic acid as represented by SEQ ID NO: 1 or a variant thereof (as defined hereinabove), which nucleic acid encodes an S3A polypeptide as represented by SEQ ID NO: 2 or a variant thereof (as defined hereinabove);
   (ii) cultivating the plant cell under conditions promoting regeneration and mature plant growth.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. Transgenic rice plants expressing an S3A are preferably produced via *Agrobacterium*-mediated transformation using any of the well known methods for rice transformation, such as described in any of the following: published European patent application EP 1198985 A1, Aldemita and Hodges (Planta, 199, 612-617, 1996); Chan et al (Plant Mol. Biol. 22 (3) 491-506, 1993), Hiei et al (Plant J. 6 (2) 271-282, 1994), which disclosures are incorporated by reference herein as if fully set forth. In the case of corn transformation, the preferred method is as described in either Ishida et al. (Nat. Biotechnol. 1996 June; 14(6): 745-50) or Frame et al (Plant Physiol. 2002 May; 129(1): 13-22), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention also includes host cells containing an isolated nucleic acid molecule encoding a protein capable of modulating an S3A protein, preferably wherein the protein is an S3A protein. Preferred host cells according to the invention are plant cells. The invention also extends to harvestable parts of a plant such as but not limited to seeds, leaves, fruits, flowers, stem cultures, rhizomes, tubers and bulbs.

The present invention also encompasses the use of nucleic acids encoding S3As and the use of S3A polypeptides.

One such use of course relates to the use of an S3A in modifying the growth characteristics of plants, in particular in improving yield, especially seed yield. The seed yield may include one or more of the following: increased number of (filled) seeds, increased seed weight, increased harvest index and increased TKW, among others. The S3A may be a nucleic acid as represented by SEQ ID NO: 1, or a variant thereof as hereinbefore defined; or the S3A may be an amino acid as represented by SEQ ID NO: 2 or a variant thereof as hereinbefore defined.

Nucleic acids encoding S3As and S3A polypeptides may also find use in breeding programmes. The S3A may be a nucleic acid as represented by SEQ ID NO: 1, or a variant thereof as hereinbefore defined; or the S3A may be an amino acid as represented by SEQ ID NO: 2 or a variant thereof as hereinbefore defined. For example, the S3A-encoding nucleic acid or a part thereof may be on a chromosome (or a part thereof), preferably together with one or more related family members. In an example of such a breeding programme, a DNA marker is identified which may be genetically linked to a gene capable of modulating expression of a nucleic acid encoding an S3A protein in a plant, which gene may be a gene encoding the S3A protein itself or any other gene which may directly or indirectly influence expression of a gene encoding an S3A protein and/or activity of the S3A protein itself. This DNA marker may then used in breeding programs to select plants having altered growth characteristics.

Allelic variants of an S3A may also be used in conventional breeding programmes, such as in marker-assisted breeding. Such breeding programmes sometimes require the introduction of allelic variations in the plants by mutagenic treatment of a plant. One suitable mutagenic method is EMS mutagenesis. Identification of allelic variants then takes place by, for example, PCR. This is followed by a selection step for selection of superior allelic variants of the sequence in question and which give rise to altered growth characteristics in a plant. Selection is typically carried out by monitoring growth performance of plants containing different allelic variants of the sequence in question, for example, different allelic variants of SEQ ID NO: 1. Monitoring growth performance can be done in a greenhouse or in the field. Further optional steps include crossing plants, in which the superior allelic variant was identified, with another plant. This could be used, for example, to make a combination of interesting phenotypic features.

Nucleic acids encoding S3As and S3A polypeptides may also find use as growth regulators. The S3A may be a nucleic acid as represented by SEQ ID NO: 1, or a variant thereof as hereinbefore defined; or the S3A may be an amino acid as represented by SEQ ID NO: 2 or a variant thereof as hereinbefore defined. Since these S3As are useful in modifying the growth characteristics of plants, the S3As would also be useful growth regulators, such as herbicides or growth stimulators. The present invention therefore provides a composition comprising an S3A, together with a suitable carrier, diluent or excipient, for use as a growth regulator.

The methods according to the present invention result in plants having modified growth characteristics, as described hereinbefore. These advantageous growth characteristics may also be combined with other economically advantageous traits, such as further yield-enhancing traits, tolerance to various stresses, traits modifying various architectural features and/or biochemical and/or physiological features.

DESCRIPTION OF FIGURES

The present invention will now be described with reference to the following figures in which:

Figure 1:
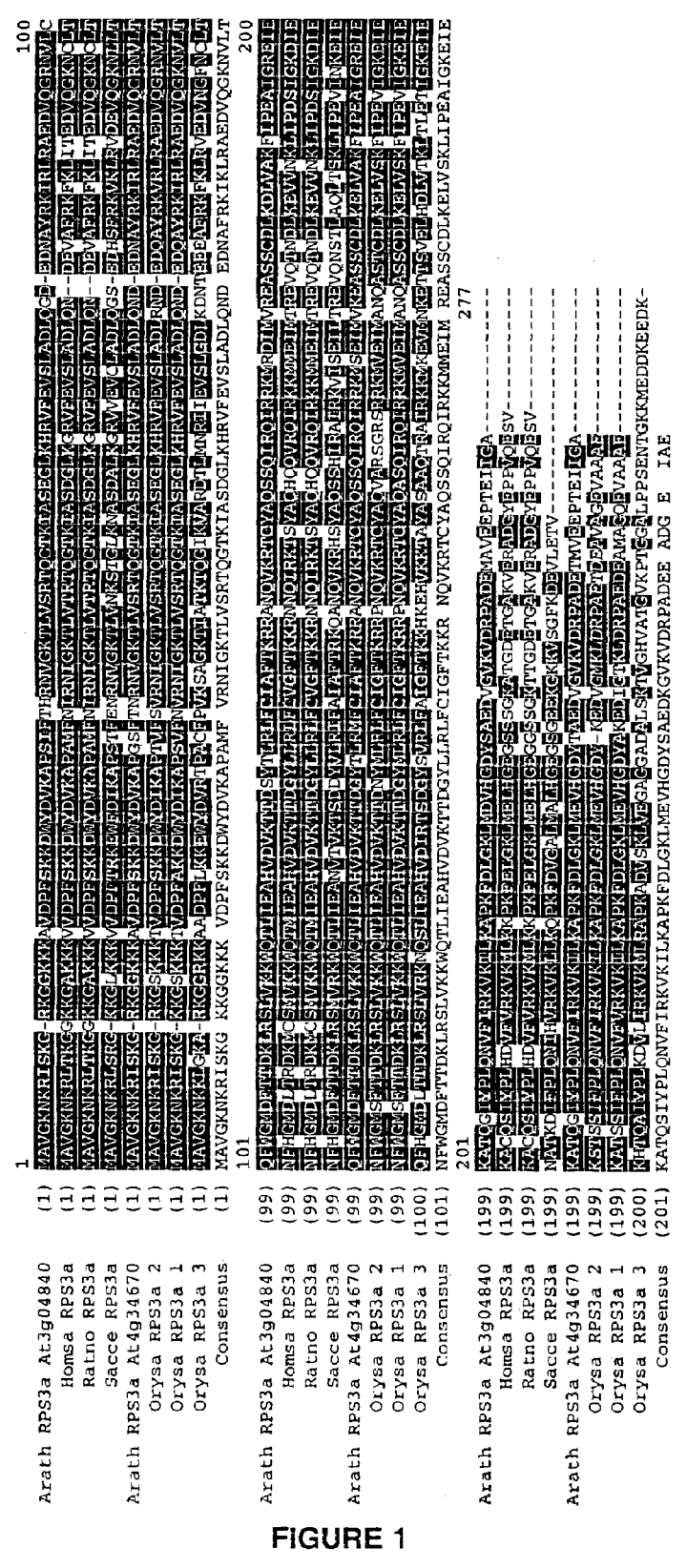

FIG. 1 shows an alignment of S3A protein sequences made using the VNTI AlignX multiple alignment program (InforMax, Bethesda, Md.), with default settings for gap opening penalty of 10 and a gap extension of 0.05. Residues appearing in white against a black background are identical; residues appearing in white against a gray background are either conservative or block of similar residues, as defined by VNTI options. (The sequences are provided in the Sequence Listing as follows: Arath RPS3a At4g34670, SEQ ID NO:2; Homsa RPS3a, SEQ ID NO:7 Ratno RPS3a, SEQ ID NO:8; Sacce RPS3a, SEQ ID NO:9; Arath RPS3a At3g04840, SEQ ID NO:10; Orysa RPS3a 1, SEQ ID NO:11 Orysa RPS3a 2, SEQ ID NO:12; Orysa RPS3a 3, SEQ ID NO:13; Consensus, SEQ ID NO:14)

FIG. 3A details examples of sequences useful in performing the methods according to the present invention. (SEQ ID NO:1, CDS0730; SEQ ID NO:2 CDS0730)

FIG. 3B details examples of sequences useful in performing the methods according to the present invention. (SEQ ID NO:3, *CSaccharum officinarum*; SEQ ID NO:4, *Saccharum officinarum*; SEQ ID NO:5, Artificial sequence prm02255; SEQ ID NO:6, Artificial sequence prm02256)

EXAMPLES

Figure 2:
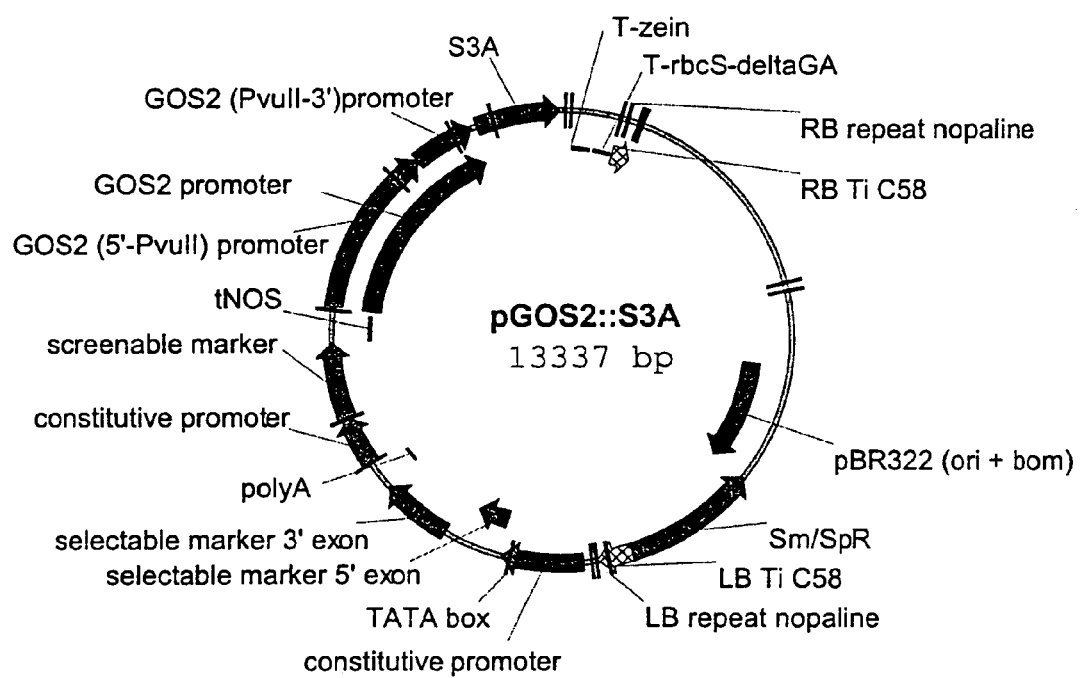
FIG. 2 shows a binary vector for expression in *Oryza sativa* of the *Arabidopsis thaliana* cyc07putative S-phase-specific 40S S3A ribosomal protein gene (internal reference CDS0730) under the control of the rice GOS2 promoter (internal reference PRO0129).

The present invention will now be described with reference to the following examples, which are by way of illustration alone.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, N.Y.) or in Volumes 1 and 2 of Ausubel et al. (1994), Current Protocols in Molecular Biology, Current Protocols. Standard materials and methods for plant molecular work are described in Plant Molecular Biology Labfase (1993) by R.D.D. Croy, published by BIOS Scientific Publications Ltd (UK) and Blackwell Scientific Publications (UK).

Example 1

Gene Cloning

The *Arabidopsis* cyc07 (S-phase specific 40S S3A ribosomal protein (internal reference CDS0730)) was amplified by PCR using as template an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was 1.5 kb, and original number of clones was of $1.59 \times 10^7$ cfu. The original titer was determined to be $9.6 \times 10^5$ cfu/ml, and became after a first amplification $6 \times 10^{11}$ cfu/ml. After plasmid extraction, 200 ng of template was used in a 50 µl PCR mix. Primers prm02255 (SEQ ID NO: 5; sense, start codon in bold, AttB1 site in italic: 5' GGGGACAAGTTTG-TACAAAAAAGCAGGCTTCACAATGGCT-GTCGGGAAGAA 3') and prm02256 (SEQ ID NO: 6; reverse, complementary, stop codon in bold, AttB2 site in italic: 5' GGGGACCACTTTGTACAA-GAAAGCTGGGTCCTAAGCTCCGATGATTTCT 3'), which include the AttB sites for Gateway recombination, were used for PCR amplification. PCR was performed using Hifi Taq DNA polymerase under standard conditions. A PCR fragment of 789 bp was amplified and purified also using standard methods. The first step of the Gateway procedure, the BP reaction, was then performed, during which the PCR fragment recombines in vivo with the pDONR201 plasmid to produce, according to the Gateway terminology, an "entry clone", p2782. Plasmid pDONR201 was purchased from Invitrogen, as part of the Gateway® technology.

Example 2

Vector Construction

The entry clone p2782 was subsequently used in an LR reaction with p0640, a destination vector used for *Oryza sativa* transformation. This vector contains as functional elements within the T-DNA borders: a plant selectable marker; a plant screenable marker; and a Gateway cassette intended for LR in vivo recombination with the sequence of interest already cloned in the entry clone. A rice GOS2 promoter for constitutive expression (PRO0129) is located upstream of this Gateway cassette. After the LR recombination step, the resulting expression vector as shown in FIG. 2 was transformed into *Agrobacterium* and subsequently into *Oryza sativa* plants. Transformed rice plants were allowed to grow and were then examined for the parameters described in Example 3.

Example 3

Evaluation and Results

Approximately 15 to 20 independent T0 rice transformants were generated. The primary transformants were transferred from tissue culture chambers to a greenhouse for growing and harvest of T1 seed. 6 events, of which the T1 progeny segregated 3:1 for presence/absence of the transgene, were retained. For each of these events, approximately 10 T1 seedlings containing the transgene (hetero- and homo-zygotes), and approximately 10 T1 seedlings lacking the transgene (nullizygotes), were selected by monitoring visual marker expression. Some T1 events were further evaluated in the T2 generation following the same evaluation procedure as for the T1 generation.

Statistical Analysis: t-test and F-test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the presence or position of the gene that is causing the differences in phenotype.

3.1 Seed-related Parameter Measurements

The mature primary panicles were harvested, bagged, barcode-labelled and then dried for three days in the oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. This procedure resulted in the set of seed-related parameters described below.

The Table of results below show the p values from the F test for the T1 evaluations, the T2 evaluations and the combined p values form the F tests for the T1 and T2 evaluations. A combined analysis may be considered when two experiments have been carried out on the same events. This may be useful to check for consistency of the effects over the two experiments and to increase confidence in the conclusion. The method used is a mixed-model approach that takes into account the multilevel structure of the data (i.e. experiment-event-segregants). P-values are obtained by comparing likelihood ratio test to chi square distributions. Each of the tables also gives the % difference between the transgenics and the corresponding nullizygotes for each generation.

3.1.1 Number of Filled Seeds

The number of filled seeds was determined by counting the number of filled husks that remained after the separation step. As shown in Table 1 below, the p value from the F test for the T1 and T2 evaluation combined was significant (with a p value of 0.0071) indicating that the presence of the construct in the plants has a significant effect on the number of filled seeds of transgenic plants.

TABLE 1

Number of filled seeds

| | % Difference | P value |
|---|---|---|
| T1 | 22 | 0.354 |
| T2 | 15 | 0.1829 |
| Combined | | 0.0071 |

3.1.2 Total Seed Yield per Plant

The total seed yield was measured by weighing all filled husks harvested from a plant. As shown in Table 1 below, the p value from the F test for the T1 and T2 evaluation combined was significant (with a p value of 0.0016) indicating that the presence of the construct in the plants has a significant effect on the total seed weight of transgenic plants.

TABLE 2

Total Seed Weight

| | % Difference | P value |
|---|---|---|
| T1 | 29 | 0.0266 |
| T2 | 20 | 0.1037 |
| Combined | | 0.0016 |

3.1.3 Harvest Index of Plants

The harvest index in the present invention is defined as the ratio between the total seed yield and the above ground area ($mm^2$), multiplied by a factor 106. As shown in Table 3 below, the p value from the F test for the T1 and T2 evaluation combined (and individually) was significant (with a p value of 0.0005) indicating that the presence of the construct in the plants has a significant effect on the harvest index of transgenic plants.

TABLE 3

Harvest index

| | % Difference | P value |
|---|---|---|
| T1 | 15 | 0.0358 |
| T2 | 14 | 0.0365 |
| Combined | | 0.0005 |

3.1.4 Thousand Kernel Weight (TKW)

This parameter is extrapolated from the number of filled seeds counted, and their total weight. As shown in Table 4 below, the p value from the F test for the T1 and T2 evaluation combined was significant (with a p value of 0.0405) indicating that the presence of the construct in the plants has a significant effect on the TKW of transgenic plants.

TABLE 4

Thousand Kernel Weight

| | % Difference | P value |
|---|---|---|
| T1 | 3 | 0.3353 |
| T2 | 2 | 0.1257 |
| Combined | | 0.0405 |

Example 4

Application of the Invention in Maize

The methods according to the invention may also be used to modify the growth characteristics of maize. An S3A is cloned under control of a constitutive promoter in a plant transformation vector suited for *Agrobacterium*-mediated corn transformation. Such vectors and methods for corn transformation have been described in literature (EP0604662, EP0672752, EP0971578, EP0955371, EP0558676, Ishida et al. 1996; Frame et al., 2002).

Transgenic plants made by these methods are grown in the greenhouse for T1 seed production. Inheritability and copy number of the transgene is checked by quantitative real-time PCR and Southern blot analysis and expression levels of the transgene is determined by reverse PCR and Northern analysis. Transgenic lines with single copy insertions of the transgene and with varying levels of transgene expression are selected for T2 seed production. Progeny seeds are germinated and grown in the greenhouse in conditions adapted for maize (16:8 photoperiod, 26-28° C. daytime temperature and 22-24° C. nighttime temperature) as well under water-deficient, nitrogen-deficient, and excess NaCl conditions.

In the case of selfing, null segregants from the same parental line, as well as wild type plants of the same cultivar are used as controls. The progeny plants resulting from the selfing or crosses are evaluated for different biomass and growth parameters, including plant height, stalk/stem thickness, number of leaves, total above ground area, leaf greenness, time to maturity, time to silking, flowering time, ear number, ear length, row number, kernel number, kernel size, kernel oil content, grain maturity, harvest time. Lines that are most significantly improved for any of the above-mentioned parameters are selected for further field-testing and marker-assisted breeding, with the objective of transferring the field-validated transgenic traits into commercial germplasm. Methods for testing maize for growth and yield-related parameters in the field are well established in the art, as are techniques for introgressing specific loci (such as transgene containing loci) from one germplasm into another. This also includes transferring a trait(s) of interest from a transformed inbred line to a commercial hybrid with desirable added agronomic or nutritional or medical value.

The invention claimed is:

1. A method for increasing seed yield in plants, comprising
   (i) introducing an expressing in a plant a nucleic acid encoding an S3A polypeptide having at least 80% sequence identity to SEQ ID NO:2,
   (ii) growing said plant expressing said nucleic acid,
   (iii) screening for plants having increased yield relative to plants of the same species that do not comprise and express said nucleic acid, and
   (iv) harvesting seeds from said plant.

2. A method according to claim 1, wherein said increased seed yield is selected from (i) increased seed biomass; (ii) increased number of (filled) seeds; (iii) increased seed size; (iv) increased seed volume; (v) increased harvest index; and (vi) increased thousand kernel weight (TKW).

3. A method for increasing plant growth rate, comprising
   (i) introducing and expressing in a plant a nucleic acid encoding an S3A polypeptide having at least 80% sequence identity to SEQ ID NO:2;
   (ii) growing said plant expressing said nucleic acid,
   (iii) screening for plants having increased yield relative to plants of the same species that do not comprise and express said nucleic acid, and
   (iv) harvesting seeds from said plant.

4. The method according to claim 1, wherein said nucleic acid encoding an S3A polypeptide is derived from a plant.

5. The method according to claim 1, wherein expression of said nucleic acid encoding an S3A polypeptide is driven by a constitutive promoter.

6. A method for the production of a transgenic plant having increased seed yield, which method comprises:
   (i) introducing into a plant or plant cell a nucleic acid selected from the group consisting of a nucleic acid as represented by SEQ ID NO: 1, a nucleic acid that encodes an S3A polypeptide as represented by SEQ ID NO: 2, or a nucleic acid that encodes a polypeptide having at least 80% sequence identity to the polypeptide sequence represented by SEQ ID NO:2;
   (ii) cultivating the plant cell under conditions promoting regeneration and mature plant growth; and
   (iii)) screening for plants having increased yield relative to plants of the same species that do not comprise and express said nucleic acid.

7. The method according to claim 4, wherein said plant is a dicotyledonous plant.

8. The method according to claim 7 wherein said plant is a plant from the Brassicaceae family.

9. The method according to claim 7 wherein said plant is an *Arabidopsis thaliana* plant.

10. The method according to claim 5, wherein said constitutive promoter is the GOS2 promoter.

* * * * *

SEQUENCE LISTING

```
<160> NUMBER OF SEQ ID NOS: 6

<210> SEQ ID NO 1
<211> LENGTH: 830
<212> TYPE: DNA
<213> ORGANISM: Arabidopsis thaliana

<400> SEQUENCE: 1
atggctgtcg ggaagaacaa gaggatttca aagggtagga aaggaggaaa gaagaaggct      60
gttgatccct tctccaagaa ggattggtat gacgtgaagg ctcctggttc tttcacgaac     120
aggaatgttg ggaagactct tgtttccagg actcagggta ccaagattgc ctctgaggga     180
ctgaaacaca gggtgtttga ggtttctctt gctgatctac aaaatgatga ggataatgcc     240
tacaggaaga tccgtcttag agctgaagat gttcagggaa ggaatgtgtt gacccagttc     300
tggggtatgg atttcacaac cgacaagcta aggtcattgg tgaagaagtg gcagactttg     360
attgaagccc atgtcgatgt gaaaaccaca gacggctaca ccttgaggat gttctgcatc     420
gccttcacaa agagacgtgc taaccaagtg aagcgtacct gttacgctca atccagccaa     480
atccgtcaga tccgcagaaa gatgagtgag attatggtga aggaggcttc atcttgtgac     540
ctcaaggagc tagtggccaa gttcatccca gaggccattg gaagagagat tgagaaggca     600
acacagggca tctacccgtt gcagaatgtg ttcatccgta aagtgaagat cctaaaggct     660
cccaagtttg accttggaaa gctcatggag gtgcatggag attacacagc agaggatgtt     720
ggtgtgaagg tagacaggcc agctgatgag acaatggttg aggagccaac agaaatcatc     780
ggagcttagg ggattataga tttgtttgtt ttttcgctgg caaaaaaaaa              830

<210> SEQ ID NO 2
<211> LENGTH: 261
<212> TYPE: PRT
<213> ORGANISM: Arabidopsis thaliana

<400> SEQUENCE: 2

Met Ala Val Gly Lys Asn Lys Arg Ile Ser Lys Gly Arg Lys Gly Gly
1               5                   10                  15
```

Lys Lys Lys Ala Val Asp Pro Phe Ser Lys Lys Asp Trp Tyr Asp Val
            20                  25                  30

Lys Ala Pro Gly Ser Phe Thr Asn Arg Asn Val Gly Lys Thr Leu Val
        35                  40                  45

Ser Arg Thr Gln Gly Thr Lys Ile Ala Ser Glu Gly Leu Lys His Arg
 50                  55                  60

Val Phe Glu Val Ser Leu Ala Asp Leu Gln Asn Asp Glu Asp Asn Ala
 65                  70                  75                  80

Tyr Arg Lys Ile Arg Leu Arg Ala Glu Asp Val Gln Gly Arg Asn Val
                85                  90                  95

Leu Thr Gln Phe Trp Gly Met Asp Phe Thr Thr Asp Lys Leu Arg Ser
            100                 105                 110

Leu Val Lys Lys Trp Gln Thr Leu Ile Glu Ala His Val Asp Val Lys
            115                 120                 125

Thr Thr Asp Gly Tyr Thr Leu Arg Met Phe Cys Ile Ala Phe Thr Lys
        130                 135                 140

Arg Arg Ala Asn Gln Val Lys Arg Thr Cys Tyr Ala Gln Ser Ser Gln
145                 150                 155                 160

Ile Arg Gln Ile Arg Arg Lys Met Ser Glu Ile Met Val Lys Glu Ala
                165                 170                 175

Ser Ser Cys Asp Leu Lys Glu Leu Val Ala Lys Phe Ile Pro Glu Ala
            180                 185                 190

Ile Gly Arg Glu Ile Glu Lys Ala Thr Gln Gly Ile Tyr Pro Leu Gln
            195                 200                 205

Asn Val Phe Ile Arg Lys Val Lys Ile Leu Lys Ala Pro Lys Phe Asp
        210                 215                 220

Leu Gly Lys Leu Met Glu Val His Gly Asp Tyr Thr Ala Glu Asp Val
225                 230                 235                 240

Gly Val Lys Val Asp Arg Pro Ala Asp Glu Thr Met Val Glu Glu Pro
                245                 250                 255

Thr Glu Ile Ile Gly
            260

<210> SEQ ID NO 3
<211> LENGTH: 1169
<212> TYPE: DNA
<213> ORGANISM: Saccharum officinarum

<400> SEQUENCE: 3
aagatgaagc ctttgtcatg gtgcatgcta aagatgctga ggctgagaag ttgagggatg      60
aaccatgaca aaggcttcat cttttctcgac ctgaatcctg tccacattcc ccttcagcat    120
cttcaattca gcctcgatca ttttcttctt aagcaccccg ccgtcgttct cttcctgcat    180
ccccgcccca ttccctagcg tcgccccct cgccgccgca cggacgcagc gacgagctct      240
cgcagcagca atggcggttg caagaataa gcgtatctcc aagggcaaga agggaggcaa      300
gaagaagacc gtggatccgt tcagcaaaaa ggattggtat gatatcaagg ctccgtcggt     360
cttcagcgtg cgcaacatcg gcaagaccct ggtctccagg acacagggca ccaagattgc     420
ctctgagggt ttaaagcaca gagtatttga ggtctccttg ctgatcttca gagtgatga     480 agaccaggcg tacaggaaga tcagacttcg tgcagaggat gtacaaggga gaaatgttct    540
cacaaacttc tggggtatga gcttcaccac cgacaagctc cgttcacttg tgaagaagtg     600
gcagacgctt attgaggctc atgttgatgt caagaccacc gataactata tgctgcggct     660

```
gttctgcatt gggttcacca agaggcggcc caatcaagtg aagcgcactt gctatgctca    720
agcaagccaa atcagacaga ttcgtcggaa gatgactgaa atcatgagca accaagcttc    780
aacttgtgat ctgaaagagc tcgtgtccaa gttcatccct gaggtcattg gaaaggaaat    840
cgagaaagcc acctctagca tattcccctt gcaaaatgtc ttcatccgca aggtgaagat    900
cctgaaagca ccaaagttcg acattggaaa gctcatggag gtccatggtg actatgccaa    960
ggaggatgtt ggtgtcaaga tggacaggcc tgctgaaggc gacgaggcca tgggaggaca   1020
ggaggttgct gcagctgagt gattagtctc actgtttacg tccgagttag agctgccata   1080
tttccttgaa acacttagga acacttttt tgagagtctg acatgtggtg gcttcgattc    1140
tccttgaaaa tttgcagcat gggaaatgt                                     1169
```

<210> SEQ ID NO 4
<211> LENGTH: 263
<212> TYPE: PRT
<213> ORGANISM: Saccharum officinarum

<400> SEQUENCE: 4

```
Met Ala Val Gly Lys Asn Lys Arg Ile Ser Lys Gly Lys Lys Gly Gly
1               5                   10                  15

Lys Lys Lys Thr Val Asp Pro Phe Ser Lys Lys Asp Trp Tyr Asp Ile
            20                  25                  30

Lys Ala Pro Ser Val Phe Ser Val Arg Asn Ile Gly Lys Thr Leu Val
        35                  40                  45

Ser Arg Thr Gln Gly Thr Lys Ile Ala Ser Glu Gly Leu Lys His Arg
    50                  55                  60

Val Phe Glu Val Ser Leu Ala Asp Leu Gln Ser Asp Glu Asp Gln Ala
65                  70                  75                  80

Tyr Arg Lys Ile Arg Leu Arg Ala Glu Asp Val Gln Gly Arg Asn Val
                85                  90                  95

Leu Thr Asn Phe Trp Gly Met Ser Phe Thr Thr Asp Lys Leu Arg Ser
            100                 105                 110

Leu Val Lys Lys Trp Gln Thr Leu Ile Glu Ala His Val Asp Val Lys
        115                 120                 125

Thr Thr Asp Asn Tyr Met Leu Arg Leu Phe Cys Ile Gly Phe Thr Lys
    130                 135                 140

Arg Arg Pro Asn Gln Val Lys Arg Thr Cys Tyr Ala Gln Ala Ser Gln
145                 150                 155                 160

Ile Arg Gln Ile Arg Arg Lys Met Thr Glu Ile Met Ser Asn Gln Ala
                165                 170                 175

Ser Thr Cys Asp Leu Lys Glu Leu Val Ser Lys Phe Ile Pro Glu Val
            180                 185                 190

Ile Gly Lys Glu Ile Glu Lys Ala Thr Ser Ser Ile Phe Pro Leu Gln
        195                 200                 205

Asn Val Phe Ile Arg Lys Val Lys Ile Leu Lys Ala Pro Lys Phe Asp
    210                 215                 220

Ile Gly Lys Leu Met Glu Val His Gly Asp Tyr Ala Lys Glu Asp Val
225                 230                 235                 240

Gly Val Lys Met Asp Arg Pro Ala Glu Gly Asp Glu Ala Met Gly Gly
                245                 250                 255

Gln Glu Val Ala Ala Ala Glu
            260
```

<210> SEQ ID NO 5

```
<211> LENGTH: 51
<212> TYPE: DNA
<213> ORGANISM: Artificial sequence
<220> FEATURE:
<223> OTHER INFORMATION: primer prm02255

<400> SEQUENCE: 5
ggggacaagt ttgtacaaaa aagcaggctt cacaatggct gtcgggaaga a          51

<210> SEQ ID NO 6
<211> LENGTH: 49
<212> TYPE: DNA
<213> ORGANISM: Artificial sequence
<220> FEATURE:
<223> OTHER INFORMATION: primer prm02256

<400> SEQUENCE: 6
ggggaccact ttgtacaaga aagctgggtc ctaagctccg atgatttct             49
```